United States Patent
Gensler

(10) Patent No.: US 9,719,952 B1
(45) Date of Patent: Aug. 1, 2017

(54) METHOD FOR MEASURING THE AMOUNT OF EXTRACELLULAR FLUID SURROUNDING A SURFACE DISPOSED WITHIN A PLANT AND THE IONIC POPULATION AND IDENTITY OF THE DOMINANT ION IN THAT FLUID

(71) Applicant: William G Gensler, Tucson, AZ (US)

(72) Inventor: William G Gensler, Tucson, AZ (US)

( * ) Notice: Subject to any disclaimer, the term of this patent is extended or adjusted under 35 U.S.C. 154(b) by 0 days.

(21) Appl. No.: 14/522,388

(22) Filed: Oct. 23, 2014

(51) Int. Cl.
   *G01N 27/22* (2006.01)
   *G01N 33/18* (2006.01)

(52) U.S. Cl.
   CPC ......... *G01N 27/22* (2013.01); *G01N 33/1806* (2013.01); *G01N 33/188* (2013.01)

(58) Field of Classification Search
   CPC .................. A61B 5/04002; G01N 33/0098
   USPC .......................................................... 324/664
   See application file for complete search history.

(56) References Cited

U.S. PATENT DOCUMENTS

| | | | | |
|---|---|---|---|---|
| 3,771,458 A * | 11/1973 | Schweimler | .......... | F42B 14/064 102/523 |
| 3,967,198 A * | 6/1976 | Gensler | .......................... | 324/72 |
| 4,021,733 A * | 5/1977 | Green et al. | ................... | 324/665 |
| 4,114,090 A * | 9/1978 | Poskitt | .......................... | 324/667 |
| 4,817,427 A * | 4/1989 | Kitano et al. | ............... | 73/204.16 |
| 4,839,581 A * | 6/1989 | Peterson, Jr. | .......... | G01R 29/24 324/450 |
| 4,952,868 A * | 8/1990 | Scherer, III | .......... | A01G 25/167 137/78.3 |
| 5,224,769 A * | 7/1993 | Holbrook et al. | ............ | 324/667 |
| 6,742,387 B2 * | 6/2004 | Hamamoto et al. | ....... | 73/335.04 |
| 6,870,376 B1 * | 3/2005 | Gensler | .......................... | 324/664 |
| 7,229,546 B1 * | 6/2007 | Gensler | .......................... | 205/792 |
| 7,956,624 B2 * | 6/2011 | Beaulieu | ....................... | 324/692 |
| 7,994,802 B2 * | 8/2011 | Osypka | ......................... | 324/692 |
| 8,111,076 B1 * | 2/2012 | Gensler | .......................... | 324/679 |
| 8,289,035 B1 * | 10/2012 | Gensler | .......................... | 324/692 |
| 2011/0288689 A1 * | 11/2011 | Kageyama | ..................... | 700/284 |

FOREIGN PATENT DOCUMENTS

WO    WO 2006121397 A1 * 11/2006

\* cited by examiner

*Primary Examiner* — Charlie Y Peng

(57) ABSTRACT

This method determines the amount of extracellular fluid surrounding a surface disposed inside a plant, the ion population in that fluid and the identity of the dominant ion in that fluid. The method has four parts: 1) Providing an electrochemical circuit between the surface and external electronics 2) Executing two electrochemical procedures which result in a sequence of measured charge transfer values, 3) Processing the measured charge transfer values into a value proportional to the of extracellular fluid surrounding the surface, a value proportional to the total ion population in the fluid and a value that identifies the dominant ion in the fluid, 4) Generating a set of time/quiescent potential pairs of values which are used to identify the dominant ion type in the extracellular fluid during different time ranges.

2 Claims, 15 Drawing Sheets

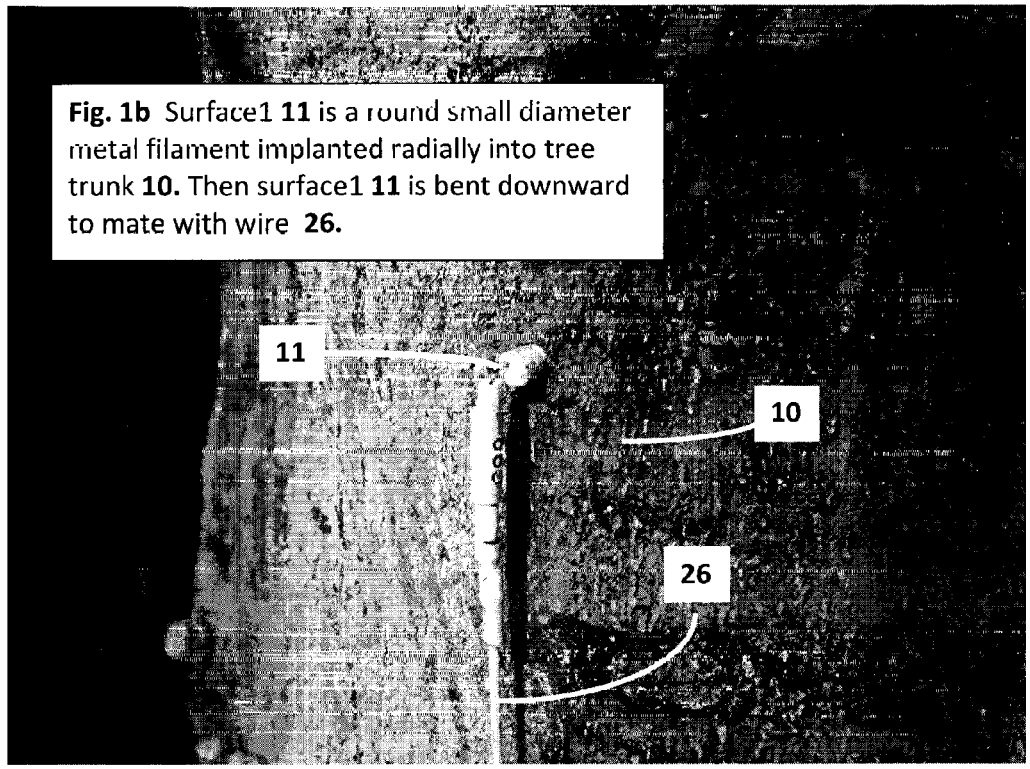

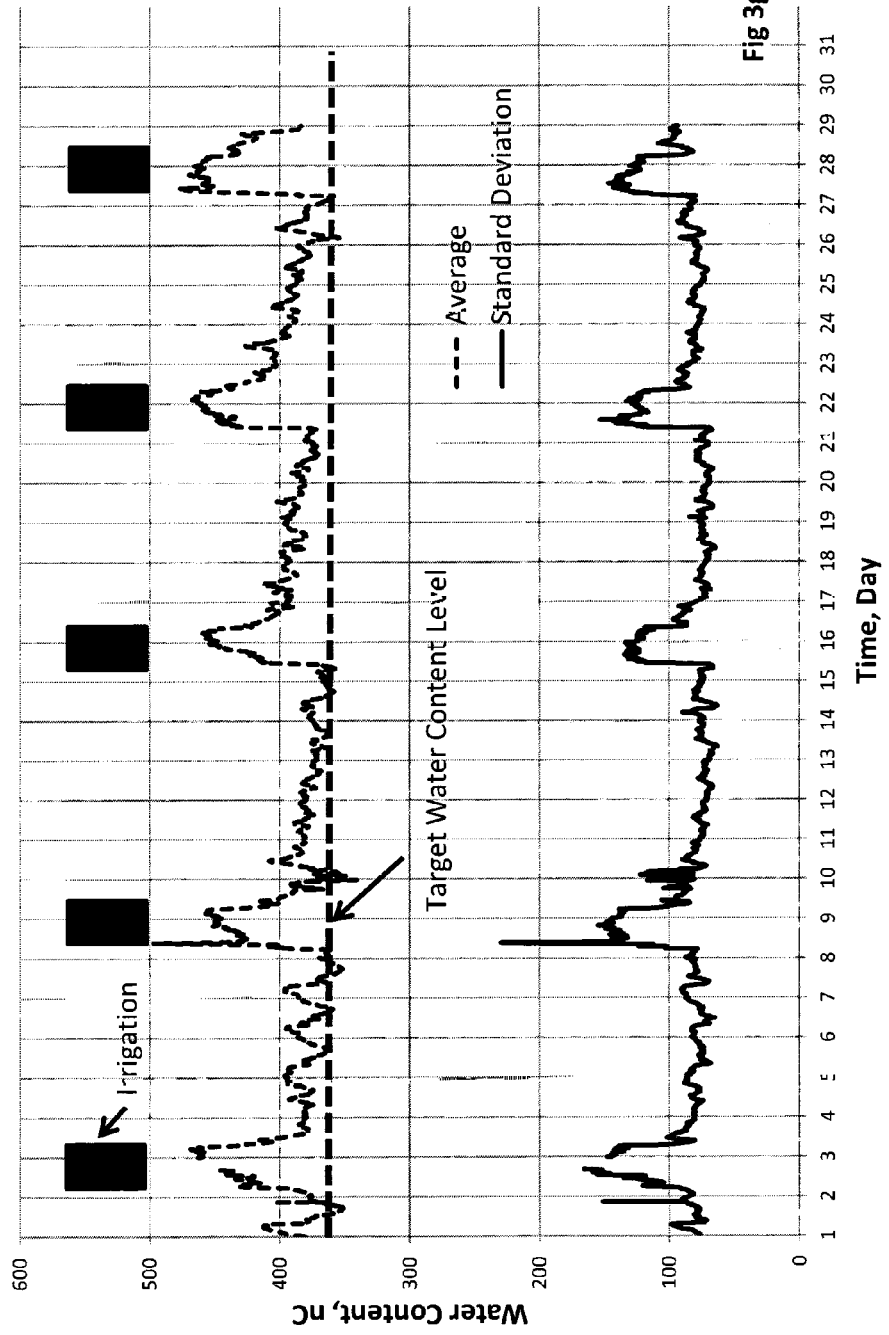

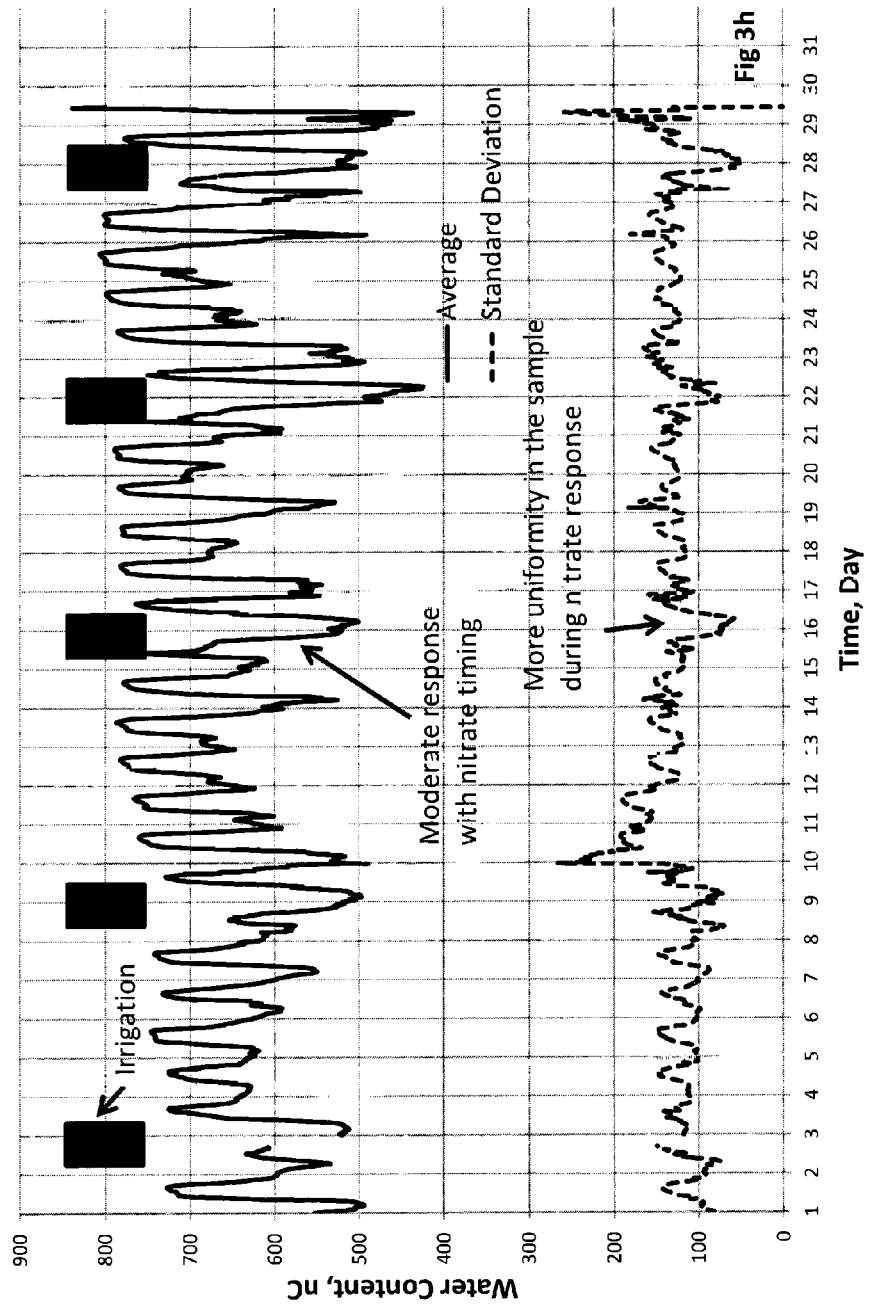

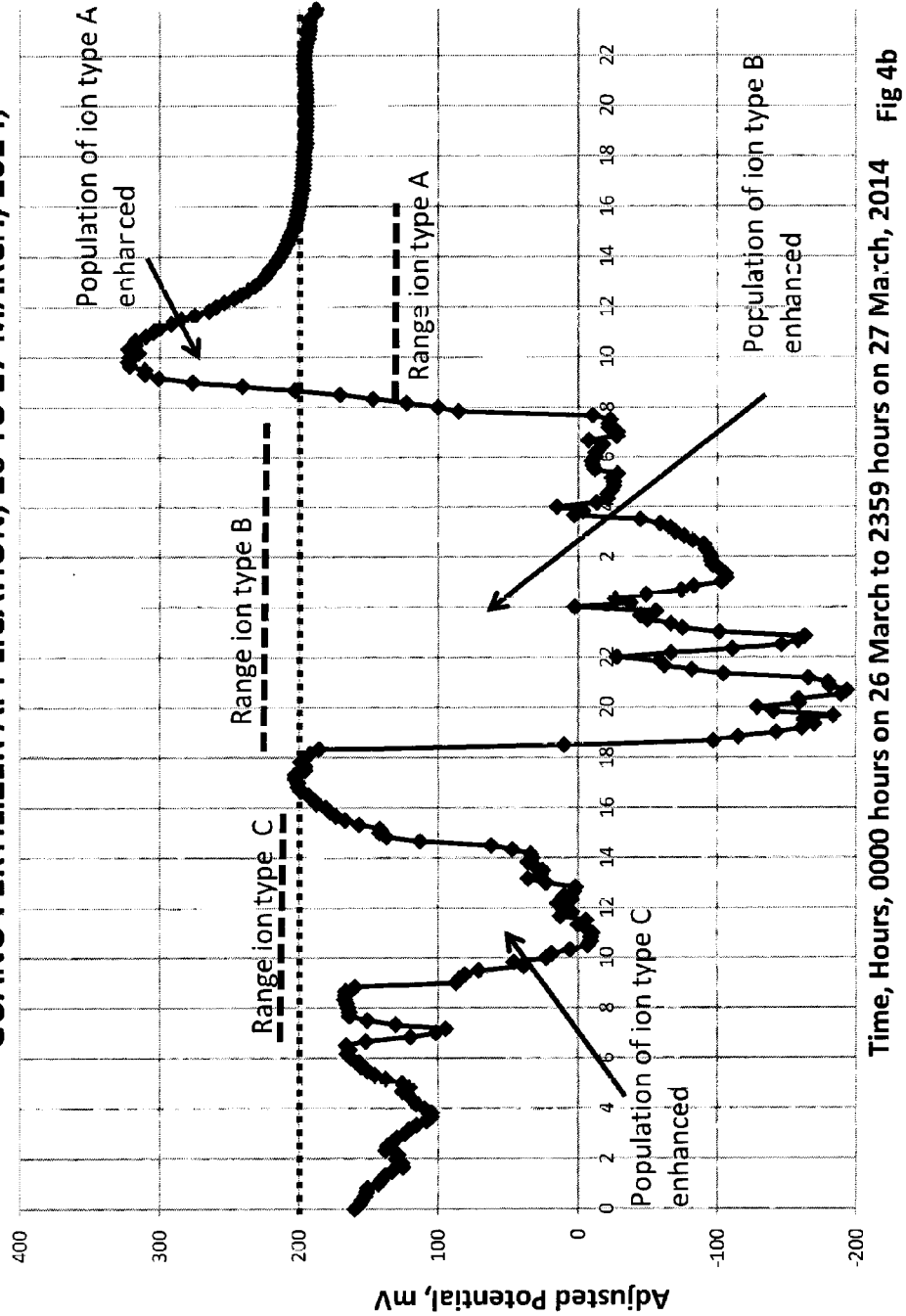

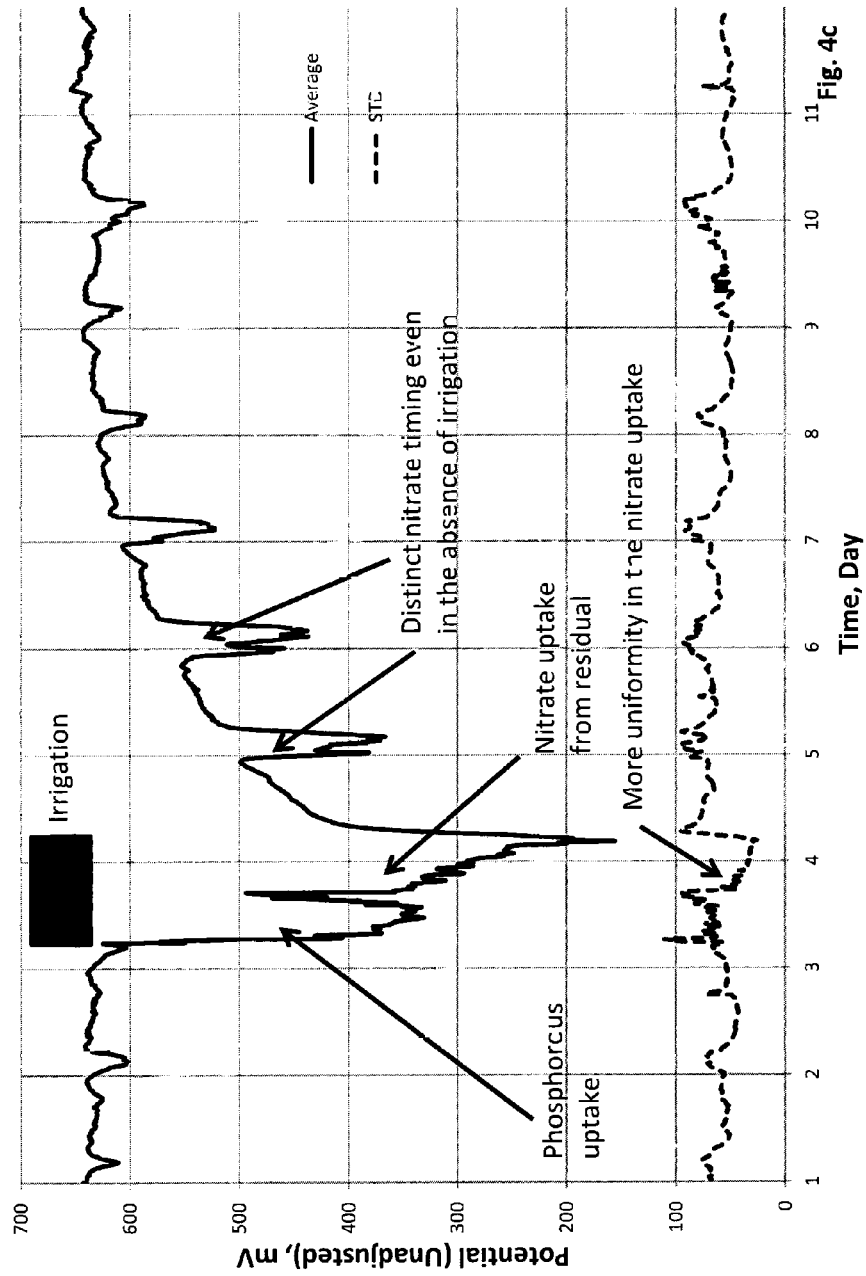

METHOD FOR MEASURING THE AMOUNT OF EXTRACELLULAR FLUID SURROUNDING A SURFACE DISPOSED WITHIN A PLANT AND THE IONIC POPULATION AND IDENTITY OF THE DOMINANT ION IN THAT FLUID

FIELD OF THE INVENTION

A method to determine in plants the extent and ionic characteristics of the extracellular fluid

REFERENCES

Bockris, J. O'M, and A. K. N. Reddy Modern Electrochemistry (1973) Plenum Publishing Company, New York.
Boylestad, R. and L Nashelsky (1977). Electricity, electronics and Electromagnetics Prentice Hall, Inc. Englewood Cliffs, N.J.
Taiz, L and E. Zeiger (2002) Plant Physiology, 3rd Edition, Sinauer Associates, Sunderland, Mass.
Bard, A. and L. Faulkner (2001) Electrochemical Methods, $2^{nd}$ Ed. Wiley, New York
Evert, R. (2006) Esau's Plant Anatomy, $3^{rd}$ Ed. Wiley, New York
Reuter, D J and J B Robinson, Eds. (1986) Plant Analysis: An Interpretation Manual, Inkata Press, Melbourne
Silva Diaz, F., W. Gensler and P. Sechaud (1983) In Vivo Cyclic Voltammetry in Cotton Under Field Conditions. J Electrochemical Society (30)7 1464-1468
U.S. Pat. No. 6,870,376 B1 2005 Method and Apparatus for Determining Plant Water Content, W. G. Gensler

BACKGROUND

Definition of Terms Employed in this Invention

Definition of the Term "Extracellular Volume"

This is the volume outside the cell membranes. It is highly sinuous. It is essentially the apoplast (Evert, Glossary, page 522) The volume has three components: air space, fluid and solid material. The magnitudes of fluid volume and air space volume change constantly.

Definition of the Term "Extracellular Fluid"

The extracellular fluid is the fluid present in the region outside cells. This includes the fluid in the xylem. It specifically excludes the fluid inside cells or the intracellular fluid. The extracellular fluid is the fluid present in the apoplast in distinction to the fluid present in the symplast (Taiz and Zeiger, Glossary, page G27)

Definition of the Term "Population"

This term refers is the number of ions in the extracellular fluid surrounding the surface disposed in the plant. For example, an ion type would be nitrate, or potassium or phosphate. Population refers to the number of nitrate inns present in a region. Since the exact volume is unknown, the term "population' is used in distinction to the term "concentration." Concentration is a defined as the population in a given volume. For example, the number of ions in one cubic millimeter or the number of ions on one square millimeter.

Definition of the Term "Capacitance"

This refers to a physical configuration of two layers of charges. There is an electrical potential across the two layers. The ratio of the charge in one of the layers to the potential across the layers is termed the capacitance, C, of the configuration. Matliemdlically, it is the ratio of charge to potential (Bard and Faulkner, Eqn. 1.2.4):

$C=Q/V$ [coulomb/volt]

In this invention a more precise definition is employed. (Bard and Faulkner, Eqn. 13.2.3):

$C=dQ/dV$ [coulomb/volt]

where "differential capacitance" is a ratio of differential charge to differential potential.

Definition of the Term "Electrochemical Procedure."

An electrochemical procedure is defined herein as a series of steps which result in measured values. These steps occur after placement of the surface in the plant, the burial of the surface in the root zone and the connection of the wires between the two surfaces and the electronics. Each individual step defines a function which must be performed by the electronics.

Definition of the Term "Potential"

The term "potential" refers to a condition between two points in space wherein one point is at a different electrical energy level than the other point. For example, point A is at an electrical energy level of plus one volt if one joule of energy is required to move one coulomb of electrical charge from point B to point A.

Definition of the Term "Mixed Potential."

The potential of a fluid that contains more than one redox couple.

Definition of the Term "Proportional,"

The term "proportional" refers to a quantitative mathematical relation between two variables. The relation does not have to be linear wherein the two variables are related by a constant. The relation can be non linear wherein the relation can take a form other than a numerical constant, for example, a polynomial.

Definition of the Term "Linear."

The term "linear" refers to a relation between two variables wherein the variables are related by a constant value. For example, if the variables Q and t are related in a linear manner then $Q=K*t$ where K is a constant value.

Definition of the Term "Dominant"

The term "dominant" refers to a part of a population wherein the characteristic of a population as a whole is set by the characteristic of this part of the population.

Prior Art Concerning Plant Anatomy and Plant Physiology

Petiole analysis is a very common procedure to determine the constituents of plant tissue. The procedure is to cut a number of leaves (or other plant parts) from the plant, grind up the leaves. Decant the fluid from the ground up mixture and then assay the constituents of the fluid. This procedure has been practiced over the entire world for decades (Reuter and Robinson, 1997). The major aspect of petiole analysis is not the procedure, but the interpretation of the results and the recommendations for fertilizer application.

The fundamental difference of this invention compared to petiole analysis is the fluid that is used in the assay. In petiole analysis, the fluid is a mixture of extracellular and intracellular fluid. Since the extracellular region is only about 5% of the total volume of the leaf tissue (Evert, R., 2006), this is mainly an assay of the intracellular fluid.

This invention is not about a mixture of the extracellular fluid and intracellular fluid. It is only about extracellular fluid. Therefore, petiole analysis and other analyses of mixtures of intra and extracellular fluid are outside the scope of this invention.

Maple syrup production has similarities to some aspects of this invention. A tube is implanted inside the tree and fluid extracted from the tree. The fluid is then distilled to increase the sugar to water ratio. Throughout this production procedure the magnitude of the sugar to water ratio is ascertained. In other words, the constituents of the fluid are ascertained.

The similarity to this invention is that a tube is implanted inside the tree. The tube is used to extract fluid from the tree. This is similar to the implanting of a surface inside the tree in this invention.

However, in this invention the surface is used to sense the amount of fluid on the surface and the constituents of that fluid while the fluid is still inside the tree. The function of the surface is to provide a metal/fluid interface for an electrochemical assay. In the maple syrup procedure, the function of the tube is to provide a vehicle for fluid extraction. There are assays of ionic constituents. The constituent of interest is the sugar population in the fluid, not the ionic populations in the fluid.

This prior art does serve to indicate several essential characteristics of this invention. A surface is implanted inside the plant. The implant procedure is non destructive. The identity and populations of the ionic constituents are determined. The fluid is assayed while the fluid is inside the plant. There is no extraction of fluid from the plant.

In summary, this prior art serves to illustrate three contrasting novel and unique aspects of this invention: 1) the procedures are non destructive, 2) the procedures are performed within the plant, that is, the procedures are non-extractive, 3) the fluid that is assayed is only extracellular fluid.

Prior Art Concerning Electrochemical Procedures
Potential Step Procedures

Potential step methods are well known among the panoply of electrochemical procedures (Bard, A. and L. Faulkner, 2001, Chapters 5, 6, 7). The procedure consists of placing a surface within a fluid. A second surface is placed in conductive contact with the first surface. The two surfaces are connected to a source of electrical potential. A potential is applied between the two surfaces. There is charge transfer as a result of this impressed potential. The magnitude of the charge transfer is measured. This procedure is similar to the procedure in this invention, that is, a potential step is applied to two surfaces immersed in a fluid and the resultant charge transfer is measured.

This method goes beyond the potential step method. In this method a surface is implanted in plant tissue in a minimally destructive manner. This surface is wetted by the extracellular fluid in the tissue. The method applies two electrochemical procedures to that surface. The method then relates the results of the procedure to water content, ion population and ion identity.

This invention differs from prior potential step procedures in another fundamental way. Identification of the ions is based, in part, on the time at which they are present in the extracellular fluid. The time at which a result is obtained is an essential part of the identification process. The identity of an anion present at one time in the twenty four hour solar cycle is different than the identity of an anion at another time in the twenty four solar cycle. Both ions are anions, but their identity is different based on when they are present. This is a unique and novel aspect of this invention. In human hematology the results of a blood test is not dependent on the time of day in which the assay is taken.

This method differs from prior art in that one of the methods of identification is based on the rate of reconfiguration of the double layer after an impressed potential is applied.

The determination of population of ion employs a base level of potential which is generated by the plant itself. This is another unique and novel characteristic of this method. The plant itself sets up the ion population in the extracellular solution and the amount of charge on the implanted surface. This is the internal homeostatic condition of the extracellular fluid surrounding the surface. The method in this invention is to determine that homeostatic charge level and perturbations of that charge due to an impressed potential.

There are no potential sweep procedures in this method such as cyclic voltammetry (Bard and Falkner, 2001 Chapter 6; Silva Diaz, Gensler and Sechaud, 1983). This is a major difference from prior art.

PRIOR ART

U.S. Pat. No. 6,870,376 B1

The method in U.S. Pat. No. 6,870,376 B1 has many similarities to this method. There is a surface within the plant and a surface in the root zone. There is electronics connected to these surfaces. The procedure employed to make a measurement in U.S. Pat. No. 6,870,376 B1 compared to this method is fundamentally different in two characteristics. In U.S. Pat. No. 6,870,376 B1, energy flow is from the plant to the electronics. In this method energy flow is from the electronics to the plant. The electronic circuitry in U.S. Pat. No. 6,870,376 B1 and this-method are completely different.

In U.S. Pat. No. 6,870,376 B1, there is no consideration of the ion constituents in the wetted fluid. They do not enter into the determination of water content. In this invention, ion constituents within the fluid are taken into account. They enter as a multiplicative factor on the value of wetted surface area. This method is a definitive advance over U.S. Pat. No. 6,870,376 B1.

SUMMARY OF PRIOR ART

Prior art is concerned with the intracellular fluid and mixtures of intracellular and extracellular fluid of plants and mainly with ex situ methods. This method is concerned only with the extracellular fluid of plants and uses an in situ method.

Prior art employs potential sweep methods wherein there is a relation between the different potential steps in a sequence (Silva-Diaz, et al). This method does not employ sweep methods.

Prior art relates a measured capacitance to tissue water content which is not potential sensitive. This method relates a measured conductance to tissue water content which is potential sensitive. Prior art employs a passive electronic method for the measurement of capacitance. This invention employs an active electronic method for the measurement of conductance.

There is no method in which the rate of reconfiguration of the double layer is employed as a method of ion identification.

Objects and Advantages

Four Parts of this Method
1. Providing for an Electrochemical Circuit
   A surface is disposed within a plant. A second surface is disposed in the root zone. Electronics is connected to the two surfaces. The surface in the plant is wetted by extracellular fluid surrounding the surface. The extracellular fluid contains ions.
2. Performing Two Electrochemical Procedures on the Electrochemical Circuit
   The result of these procedures is a quiescent potential value and a sequence of charge values.
3. Processing the Charge Values Obtained from the Electrochemical Procedures
   The sequence of charge values from Part Two are processed (separated) into two sequences of charge values that give the amount of extracellular fluid on the surface, the total ion population within that fluid and the identity of the dominant ion in that fluid.
4. Repeating the Electrochemical Procedures Multiple Times Over an Extended Time Period
   The result is a set of pairs of time values and potential values. These pairs are used to identify the dominant ion type and the relative population of the dominant ion type in the extracellular fluid. The procedures are performed over a time scale of hours, days and weeks.
1. Providing for an Electrochemical Circuit
   The apparatus that must be provided for is shown in FIG. 1a. There are four basic components: an electrochemically active surface 11 resident in the extracellular volume inside the plant, a surface 12 located in the root zone, a reference surface 12 located in the root zone and electronics 29 connected to these surfaces. This method employs these four components to achieve the following objectives: 1) measurement of amount of fluid in the region around the surface 11, 2) measurement of the identity of the ions within that fluid and 3) measurement of the population of ions within that fluid.

FIG. 1b gives an example of the surface 11 implanted in the trunk of a citrus tree. The surface consists of a round metal filament bent at a right angle such that it is implanted radially into the sapwood of the trunk. Only the part of the surface outside the tree is visible. A wire at the bottom connects the surface to electronics.

The quintessential part of the physical components in FIG. 1a and FIG. 1b is the interface 14 between the metal surface inside the plant and the fluid that surrounds the surface. From an anatomical viewpoint, this metal/fluid interface is located in the apoplast, that is, the region outside the cells. The fluid is apoplastic or extracellular fluid. Metabolic activity in the cells in the vicinity of the interface cause constant changes in the amount of fluid present and the constituents within the fluid. Many of these constituents are ions. This method focuses on these ions. This method quantifies how much fluid is present and the identity and population of the different ion types. This provides quantification of the physiological activity that requires the presence of the different ion types.

From an electrochemical viewpoint, the metal/fluid interface 14 is a configuration of two charge layers. One charge layer $Q_{DL}$ consists of ions in the fluid contiguous to the surface. The second charge layer is electrons at the surface of the metal. This interface has a potential across the two charge layers. The interface charge layers can be described in terms of a fluid capacitor. This capacitor relates charge to potential. The relation between the charge and potential is dependent on the types of ions present and their populations in that fluid.

The metal/fluid interface 14 is also the site of charge transfer between the metal and the bulk fluid 36.
2. Performing Two Electrochemical Procedures on the Electrochemical Circuit
   This method has two electrochemical procedures. The first procedure has a single step and one measurement: measurement of the quiescent potential. The second procedure has a single step as well. But there are two measurements: measurement of the quiescent potential, application of a perturbation potential and measurement of the charge transferred as a result of this perturbation potential.

The quiescent potential is a mixed potential. A mixed potential is a potential across a metal/fluid interface that is the result of the presence of more than one redox couple, or reactants in the solution. It is potential measured at zero net current across the interface. In the situation under discussion, the extracellular fluid contains more than one reactant. The potential arises from the combined influence of all the reactants in the fluid.

The second procedure includes the first procedure but the measured quiescent potential is perturbed about the quiescent potential and the perturbation potential is impressed on the terminals of the electrochemical cell. This results in a charge transfer during the period of application of the perturbation potential.

Charge transfer can be measured by the electronics. The charge transfer consists of electrons that are a result of a transfer of electrons across the interface $Q_F$ and electrons that are result of a reconfiguration of the double layer of charge at the metal/fluid interface $Q_{DL}$. By a determination of the time and magnitude of the electron transfer it is possible to separate out these two sources of electrons because the electrons from each source are superimposed on each other. In general, the rate of electron transfer from a movement of electrons across the interface is constant in time during the duration of the perturbation potential. The reconfiguration of the double layer is first order exponential in its time variation. Separation is possible if one makes measurements during the exponential rise and after the time when the exponential has reached a near final terminal value. In spite of a reconfiguration of different reactants, a single exponential is present characterized by a single time constant and final value. Changes in the relative magnitudes of the populations of the ions present are manifest in a change in the final value of the exponential and also the time constant of the exponential. These two characteristics are used in this invention to identify the type of ions present and their relative magnitudes. Ions reconfigure at different speeds. A short time constant is indicative of a presence of a relatively large population of a "faster" ion. A long time constant is indicative of the presence of a relatively large population of a "slower" ion. The time constant yield a quantitative measure of the relative proportions of the different ion types.

Interfacial Potential and Cell Potential

Electrochemical circuits always involve two electrodes and path between the two electrodes. There is an interface at both electrodes. The potential across either interface can change. The interface of interest is the electrode/tissue interface in the plant. In order to insure that changes in the other electrode interface do not enter into the calculations, a reference surface is added to the circuit. This surface has the characteristic that the interfacial potential of this electrode with the root zone does not change. The method in this invention using these three surfaces will now be discussed.

Electrochemical Procedure #1: Measurement of the Quiescent Potential

The first electrochemical procedure is the measurement of the quiescent potential. Quiescent potential is the potential that is present across the terminals of the two wires connected from surface1 11 inside the plant and surface2 12 located in the root zone to the electronics. There is a special circumstance associated with the measurement of this potential. It is made when there is no significant charge transfer through the wires. That is reason for the term "quiescent." The pathway between these two surfaces has two interfaces, a metal/extracellular fluid interface and a metal/root zone interface. The potential across each of these two can change. But the interface of interest Is the metal/extracellular fluid interface. It is necessary to insure a situation where changes in the potential across the metal/root zone interface have no influence. To accomplish this, surface3 13 is placed in the root zone. This surface has the characteristic that the interface between surface3 and the root zone does not change. Surface3 13 functions as a reference surface.

In the following equations, the dimension of the variable is given, for example, volts or millimeters or coulombs. This is done only to enhance the reader's understanding by making the equation more tangible. The equations are not dependent on a particular set of dimensions.

Potential measurements are now made as follows:

$$V_{S1} - V_{S2} = M1 \; [\text{millivolt}] \quad (1)$$

$$V_{S3} - V_{S2} = M2 \; [\text{millivolt}] \quad (2)$$

Eqn. 1 states that a voltmeter placed across electronics terminal1 and electronic terminal2 yields a value of M1. Eqn. 2 states that a voltmeter placed across electronics terminal3 and electronic terminal2 yields a value of M2. Subtracting Eqn. 2 from Eqn. 1 yields $$V_{S1} - V_{S3} = M1 - M2 \; [\text{millivolt}] \quad (3)$$

Eqn. 3 states that the potential of surface1 with respect to surface3 is equal to the value of M1 minus the value of M2.

Surface3 is a reference surface or reference electrode which has a constant potential across the electrode root zone/interface. This results in a value of potential of surface1 that is independent of any changes in the potential across the surface2/root zone interface. The "adjusted value of $V_{S1}$" becomes $$V_{S1} = M1 - M2 + V_{S3} \; [\text{millivolt}] \quad (4)$$

It is possible to a move a step further and consider the potential of surface S3 with respect to the standard hydrogen electrode $$V_{S3} - V_{SHE} = M3 \; [\text{millivolt}] \quad (5)$$

Then adding Eqn. 4 and Eqn. 5 yields $$V_{S1} - V_{SHE} = M1 - M2 + M3 \; [\text{millivolt}] \quad (6)$$

Eqn. 6 gives the value of the potential of surface1 with respect to the standard hydrogen electrode in terms of two measured values M1 and M2 and a fixed value, M3. The potential $V_{S1}$ defined in Eqn. 1 can be used if $V_{S2}$ is near constant over the duration of the measurements. If not, the potential $V_{S1}$ defined by Eqn. 6 can be used.

Description of the Physical and Chemical Characteristics of the Fluid Wetting the Surface within the Plant FIG. 2a gives a top view of the wetted area on surface1 11 inside the plant. The physical and chemical characteristics of this wetted area are illustrated in the side view in FIG. 2b. It consists of a layer of fluid 34 containing ions. Opposite to this layer of ions is a layer of electrons 35. These two layers form a double layer of charge. Bulk fluid 36 is just above this double layer. Bulk fluid 36 is a region where the positive and negative ions coexist at the same concentration as the surrounding extracellular fluid.

FIG. 2c illustrates the population of adsorbed anions 44 and cations 43 within a tiny square area of wetted surface 41. If the population is dominated by anions such shown at the bottom square in FIG. 2c, then the potential, $V_{S1}$ is more negative. If the population is dominated by cations such as shown in the top square in FIG. 2c, then the potential, $V_{S1}$ is more positive. The value of potential $V_{S1}$ gives an indication of the relative population of anions and cations.

The situation shown in FIG. 2c is an equilibrium or quiescent mode. There is no net charge transfer across interface1 14. The ion populations are stable. The electrochemical circuit is neither a galvanic cell nor an electrolytic cell. The electronics measures the potential of terminal1 17 with respect to terminal2 18. The result is a potential referred to as the "quiescent potential."

FIG. 2d illustrates the shift in adsorbed ion population due to a positive potential impressed on terminal1 17 with respect to terminal 18 which is higher than the quiescent potential. This is illustrated in the potential axis in FIG. 2d as a shift toward a positive potential. This causes positive ions to move from interface1 14 to the bulk fluid 36 and negative ions to move from the bulk fluid 36 to interface1 14. The result of this shift is shown in the shift in ion population in the squares in FIG. 2d.

Electrochemical Procedure #2: Measurement of Charge Transfer Due to Application of a Perturbation Potential about the Quiescent Potential The second electrochemical procedure is the application between terminal 1 and terminal2 of a perturbation potentials for a short period of time. This causes charge $Q_M$ to flow between terminal1 and terminal 2 of the electronics. FIG. 2e illustrates the sequence of values of charge $Q_M$ measured over the duration of the perturbation potential.

Results of the Two Electrochemical Procedures

Electrochemical Procedure #1 results in a single potential value, $V_{S1}$. Electrochemical procedure #2 results in a sequence of values of charge, $Q_M$ measured over the duration of the perturbation potential.

3. Processing the Charge Values Obtained from the Electrochemical Procedures

Processing the individual values, $Q_M$, in the sequence of charge transfer valuesM consists of separating each value into the part due to transfer of adsorbed ions and a part due to electrons crossing interface2. These charge transfers are additive and can be expressed in the following relation $$Q_M = K^* t + M(1 - \exp(t/TC)) \; [\text{nanocoulomb}] \quad (7)$$

where the measured charge transfer is $Q_M$, valueM; M(1−exp(t/TC))) is the charge transfer due to reconfiguration of the adsorbed ions, valueDL; $K^*t$ is the charge transfer due to electrons crossing interface1 14, valueF.

The electron transfer across interface1 14 during the period of impressed potential increases in a linear manner. The value of K can be determined from the slope of the values of $Q_M$ in the period of time during which the change in the adsorbed ion population on the wetted surface is negligible.

FIG. 2e gives a graphic example of these three values for periodic measurements of $Q_M$. This relation can be extended to a respective relation between the sequence of charge transfer valuesM and two other sequences: sequence of charge transfer valuesDL and sequence of charge transfer valuesF. In other words, the respective values in these latter sequences are additive and equal to the value in the sequence of charge transfer valuesM. The three sequences in FIG. 2e are an example of this additivity.

Summary of the Processing of Individual Values of the Sequence of Charge Transfer ValuesM The result of the processing of sequence of charge transfer valuesM is two sequences: sequence of charge transfer valuesDL which are values of change in the adsorbed ion population and sequence of charge transfer valuesF which are values of the change in the population of electrons which cross interface1 during time interval T1. These sequences add respectively to yield the sequence of charge transfer valuesM.

Physical Significance and Utility of the Value of K*t in Eqn. 7

The physical significance of the product, K*t, that is, valueF, is based on the proportionality of valueF to the wetted area of surface1 11. As the amount of fluid in the extracellular volume increases and decreases, valueF increases and decreases in concert.

Physical Significance and Utility of the Value of M in Eqn. 7

The physical significance of M in Eqn. 7 is based on the proportionality of the value of M to the total ion population in the bulk fluid surrounding surface1 11.

Physical Significance and Utility of the Value of the Time Constant, TC in Eqn. 7.

Eqn. 7 indicates the total ion population changes due to the imposition of the perturbation potential. Ions move between the bulk extracellular fluid and the surface. The change is not instantaneous. The rapidity of the ion movement depends in the type of ion, small ions move faster than big ions. Some ions have a hydration shell of water molecules around them and these molecules must be dragged along. Nitrate ions move quickly. Potassium ions move slowly. If there is a large majority population of slowly moving ions, the reconfiguration takes a long time. This is manifest in a large time constant. By contrast, if there is a large majority of fast moving ions in the population, the reconfiguration is rapid. This is manifest in a short time constant. The time constant can then be used to identity the ion type that dominates the rapidity of ion movement.

This is an analog indicator, that is, there is a continuum of values of the time constant, from very short to very long. At some point in the middle of the continuum, the ion populations are balanced. The time constant gives an indication of a deviation from this balance and identifies the ion type contributing to an unbalance.

Summary of Processing Raw Measured Charge Transfer Values into Variables with Physical and Chemical Significance The sequence of measured charge transfer value, $Q_M$, is processed into five cardinal values. These values quantify the amount of extracellular fluid surrounding surface1 11, total ion population in that fluid and identity of the dominant ion in that population. Table 1 summarizes the five values

TABLE 1

Cardinal Values: Their Significance, Mathematical Description, Correlated Drawings and Subsequent Claim Step

| Cardinal Value, Units | Physical and/or Chemical Significance | Mathematical Description |
|---|---|---|
| Water Content, nanoCoulomb | Amount of Extracellular Fluid Surrounding Surface1 (11) | Eqn. 7; FIG. 2e, FIG. 3e, FIG. 3g; Claim 7, Step (i) |
| Total Ion Population, nanoCoulomb | Total Anion and Cation Populations in the Extracellular Fluid Surrounding Surface1 (11) | Eqn. 7; FIG. 2a through 2d; FIG. 2e; Claim 7, Step (j) |
| Time Constant, millisecond | Identifier of the Dominant Ion Type in the Population of ions in the Extracellular Fluid Surrounding Surface1 (11) | Eqn. 7; FIG. 2e; Claim 7, Step (j) through (m) |
| Ratio: Total Ion Population/Water Content, numeric | Indicates relative composition of Ion Types Contributing to Double Layer and ion types contributing to electron transfer; independent of wetted area | M/(K * t) |
| Quiescent Potential, mV | Energy Level of the Ion Population in the Extracellular Fluid Surrounding Surface1 (11). Used as an Identifier of the dominant Ion Type | Eqn. 1 through Eqn. 6; FIG. 2c, FIG 3b, FIG. 3d, FIG. 3f, FIG. 3h; Claim 8 |

The method is not dependent on a system of units such as nanocoulombs, mV, etc. These unit are given only to enhance understanding of the physical and chemical significance of the values.

Examples of the Cardinal Values

FIG. 3a is a schematic illustration of values of $Q_{DL}$ as a result of multiple executions of the two electrochemical procedures of a diurnal cycle. There is a rise in the total ion population at post dawn. This increasing trend continues until mid day at which time the population reaches a maximum. The value plateaus until late afternoon and then begins a slow decline until just before dawn.

The rise at dawn is due to an extrusion of water and ions from living cells surrounding surface1 11 in the post dawn hours. Mid day is characterized by a metabolic plateau. Recharge of water and ions into the cells begins in the late afternoon. This recharge continues until dawn the next day.

Concomitant with this water and ion cycle, there is a cycle of quiescent potential shown in FIG. 3b. The potential decreases at post dawn. It then reaches a minimum level and remains at this minimum level for several hours. It then rise back to the pre dawn level. The changes in water content and potential is due to ion changes in the immediate vicinity of surface1. This is known as the local mode.

FIGS. 3c and 3d is a schematic illustration of multiple diurnal cycles with a strong deviation of the charge and potential patterns due to passage of water and ions through the vicinity of surface1 11. This pattern illustrates the short term presence of non-local ions and water in the vicinity of surface1 11. Water and ions which are local to the region of surface1 11 set the pattern during the local mode. But this local mode pattern is disturbed as a surge of non-local water and ions mixes with the extracellular fluid surrounding surface1.

FIGS. 3e and 3f illustrate this same set of patterns in almonds subjected to two twenty four hour irrigations. The local mode diurnal cycles are disturbed due to the plant taking up irrigation water. The values of water content during the actual irrigation period is not uniform. This indicates the plant is selective about the timing of its response. The level of water content following each irrigation changed. This indicates the plant took up and retained water following the water application period. This is an expected response since the trees were in a water deficit mode in late August due to harvesting operations. The potential patterns in FIG. 3f responded to the irrigation but there was no increase in level in the post irrigation period. Both the water content and potential pattern timing in the local mode was unchanged as a result of the irrigations.

FIGS. 3g illustrate a contrasting pattern in avocados. There were six twenty four hour irrigation cycles. The water content patterns illustrate a short term rise in water content and then a gradually decreasing water content level in the period between irrigations. The minimum level of water content would be an indication of a target level on the part of the Grower. FIG. 3h illustrates relatively modest but consistent responses. The potential distinctly decreases during the nighttime hours indicative of nitrate uptake.

4. Repeating the Electrochemical Procedures Multiple Times Over an Extended Time Period Execution of the Electrochemical Procedures periodically 24/7/52 provide an indication of water and nutrient activity of the extracellular fluid during a single diurnal cycle as well as variations over the growth and reproductive cycles. Identification of the dominant ion type can be obtained using simultaneous measurements of time and quiescent potential. The background to this identification method will now be discussed Background The plant is highly selective about the type of ions present and when they are present in the extracellular region. It appears, only one type of ion is moved into the region during any particular period. These characteristics are utilized in a second ion identification method. Identification is based on polarity and timing. This is novel part of this method compared to normal electroanalytical identification procedures. In normal ex situ electroanalytical procedures, the procedure can be carried out in the morning or afternoon. For example, human blood tests are not time sensitive. The time of execution is not important. In this method, time is important. The procedure is accomplished in situ. The fluid is not extracted from the plant but remains in the plant. The time at which the procedure is executed is part of the method of identification.

Basic Identification Method

The basic method is to execute Electrochemical Procedure #1 at fixed time intervals over a solar cycle. This generates pairs of values, a time valueX and a potential valueX. The symbol X indicates that it is one member of the set of pairs. The measurements begin at an onset time and end at a termination time. For example, onset time could be 0800 hours and termination time could be 0800 hours the next day.

The next step in the method is to set a reference potential value which is constant throughout the solar cycle.

The next step is to form four group, groupA, groupB, groupc and groupD. The data pairs generated in the execution of Electrochemical Procedure #1 will be placed in each of these groups if the time valueX and potential valueX satisfy a time criterion and a potential criterion for each group. The groups are empty at this time.

The next step in the method is to form four time ranges: time rangeA, time rangeB, time rangeC and time rangeD. These are intervals of time between the onset time and the termination time. The only limitation on the time ranges is that two of them, time rangeA and timeD are mutually exclusive, that is, the time values in time rangeA are not included in time rangeD. For example, time rangeA might extend from 0800 hour to 1400 hours, time rangeD would extend from 1400 hours to 0800 hours the next day. Furthermore, time range B and time rangeC are also mutually exclusive. For example, time rangeB might extend from 0800 hours to 1600 hours. Time rangeC would extend from 1600 hours to 0800 hours the next day.

The next step in the method is to apply a criterion to the time value and criterion to the potential value in each pair and place the pair in the group wherein both criteria are satisfied. For example, to be placed in groupA, the time value must be within the time range of groupA and the potential must be greater than the reference potential. If these two criteria are satisfied the pair is placed in groupA.

The criteria for each group are summarized in Table 2 below

TABLE 2

Grouping of Ions according to Ion Type and Qualification Criteria

| Group | Time Criterion | Potential Criterion |
|---|---|---|
| GroupA | time valueX within time rangeA | potential valueX greater than reference potential |
| GroupB | time valueX within time rangeB | potential valueX less than reference potential |
| GroupC | time valueX within time rangeC | potential valueX less than reference potential |
| GroupD | time valueX within time rangeD | potential valueX greater than reference potential |

Each group now contains pairs of time values and potential values that satisfy the required criteria.

The next step in the method is to generate a value which is the sum of the the relation (for a member of groupA)

$$\text{sum}AX = V_{S1}(AX) - \text{reference potential} \tag{8}$$

where $V_{S1}(AX)$ is a potential valueX which has been placed in groupA

The term sumAX replaces potential valueX.

Eqn. 8 is repeated for all potential values in each pair in the four groups. The result is that each group now contains pairs of time values and sum values.

The next step in the method is to add together all the sum values. The result is a total sum value for each group. The magnitude of this total sum value indicates the presence of a particular ion type. For example, the absolute value of total sumC indicates the presence of ion type C.

The term "presence" can be interpreted numerically. A high absolute value of total sum indicates a high population of the particular ion. A low absolute value indicates a low population of the particular ion.

The term "presence" can be interpreted in terms of the polarity of the ion. A high negative value of the total sum indicates a strong presence of anions. A high positive value of total sum indicates a strong presence of cations.

The Method in Terms of an xy Plot

These steps can be visualized in terms of the two dimensional xy plot shown in FIG. 4a. Time is presented on the x axis and quiescent potential is presented on the y axis. The vertical axis is divided by the homeostatic quiescent potential, $V_R$. Values of potential more positive than $V_R$ are above the horizontal axis. Values more negative than $V_R$ are below the horizontal axis. Identity of the type of ion in the extracellular fluid is accomplished in this method by using two characteristics of the ions: quiescent potential and the time at which the ion is present in the fluid. This leads to an integral part of the identification method. The passage of time is divided into ranges. For example, a range would begin at 1700 hours and ends at 0800 hours the next morning. Another range may begin at 0830 hours in the morning and end at 1600 hours in the afternoon. The only restriction on these ranges is that they do not overlap. For example, nitrate and phosphate ions are both anions. But the range of time during which nitrate is present does not overlap with the range of time during which phosphorous ions are present. Polarity is also part of the method of identification. Positive charge causes a more positive quiescent potential. Negative charge causes a negative quiescent potential. The dividing line between the polarity of the quiescent potential is the reference potential. FIG. 4b illustrates an example of the time/potential diagram in FIG. 4a following application of guano fertilizer to lemon trees The tree distinctly separates out the response into three time ranges, two anion ranges and one cation range. Experience with other fertilizer application indicates ion type A was phosphorous; ion type B was nitrate and ion type C was potassium.

FIG. 4c illustrates an example of the potential response following the application of phosphoric acid through the drip lines in a pecan block. This response clearly indicates the plant separates uptake into two time intervals. Phosphorous taken up during the mid day period. The potential distinctly increases. Following this the potential decreases again. This is a transition period wherein the plant shifts from a phosphorous uptake period to a nitrate uptake period. Uptake is divided into two different time ranges or periods. This is the basis for the ranges shown in FIG. 4a. The examples in FIG. 4b and FIG. 4c illustrate the distil tendency on the part of the plant to take up one type of ion at a time.

OPERATIONAL DESCRIPTION OF THE METHOD

List of Reference Numerals 10 plant
11 surface1 resident in the extracellular volume inside the plant
12 surface2 resident in the root zone
13 surface3 resident in the root zone
14 interface1
17 terminal1 of the electronics
18 terminal2 of the electronics
19 terminal3 of the electronics
21 root zone
26 first wire connecting surface1 to terminal1
27 second wire connecting surface2 to terminal2
28 third wire connecting surface3 to terminal3
29 electronics
30 path of charge movement between surface1 and surface2
33 wetted area, $A_W$, on surface1
34 layer of ions adsorbed on surface1
35 layer of electrons on surface1
36 bulk fluid
43 Cation
44 Anion
47 Potential of balanced charge, $V_{PBC}$

BRIEF DESCRIPTION OF DRAWINGS

FIG. 1b Example of surface1 (11) disposed within a plant 10. Surface1 11 is a round metal filament implanted into homogeneous xylem for an active length of ten millimeters.

FIG. 3g Example of the sapwood water content response to irrigation in avocados.

The water content level jumped with irrigation and then gradually dropped off in the post irrigation period.

Figure 3A:
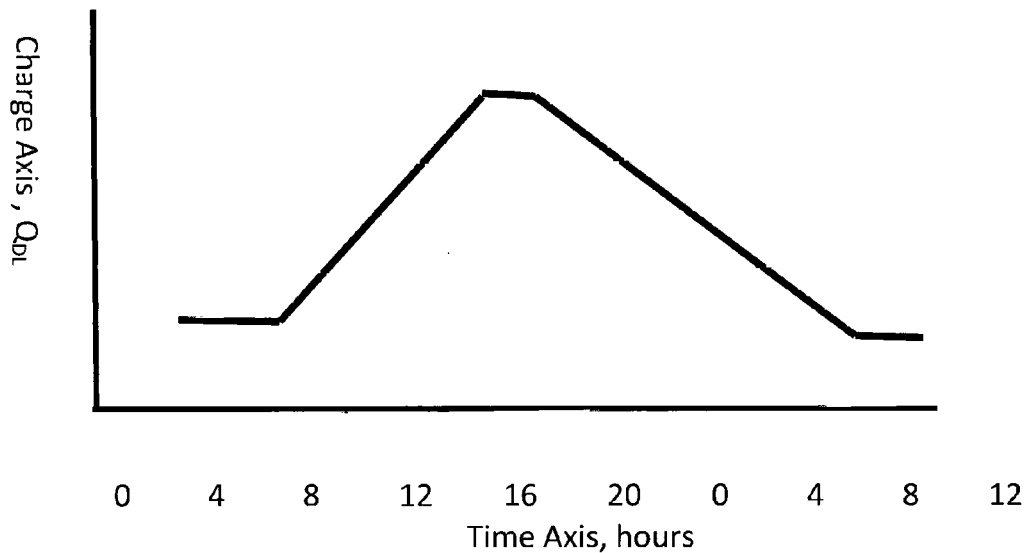
FIG. 3a Schematic diagram of the total adsorbed ion population measured over a diurnal cycle. Although shown as a continuous line, the population is measured at discrete time intervals such as every half hour. The value shown are the double layer charge transfer, $Q_{DL}$. The source of the differences are the extrusion and recharge of ions from and to living cells in the immediate vicinity of surface1.
Figure 3B:
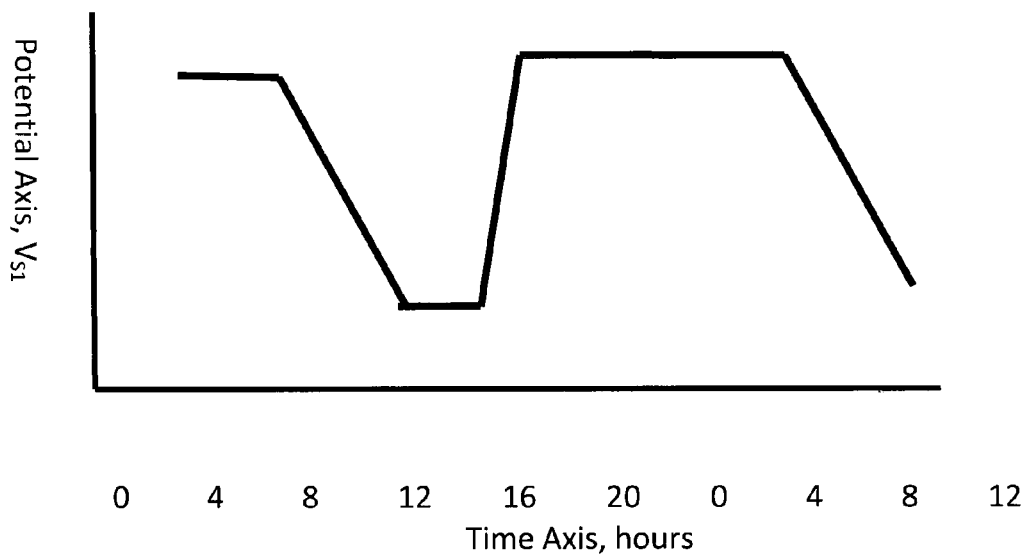
FIG. 3b Schematic diagram of the quiescent potential measured over a diurnal cycle in the local mode. The adsorbed ion population shifts during the cycle and so does the composition of ions within the population. This shift in composition is manifest in a shift in energy level of the population as a whole.
Figure 3C:
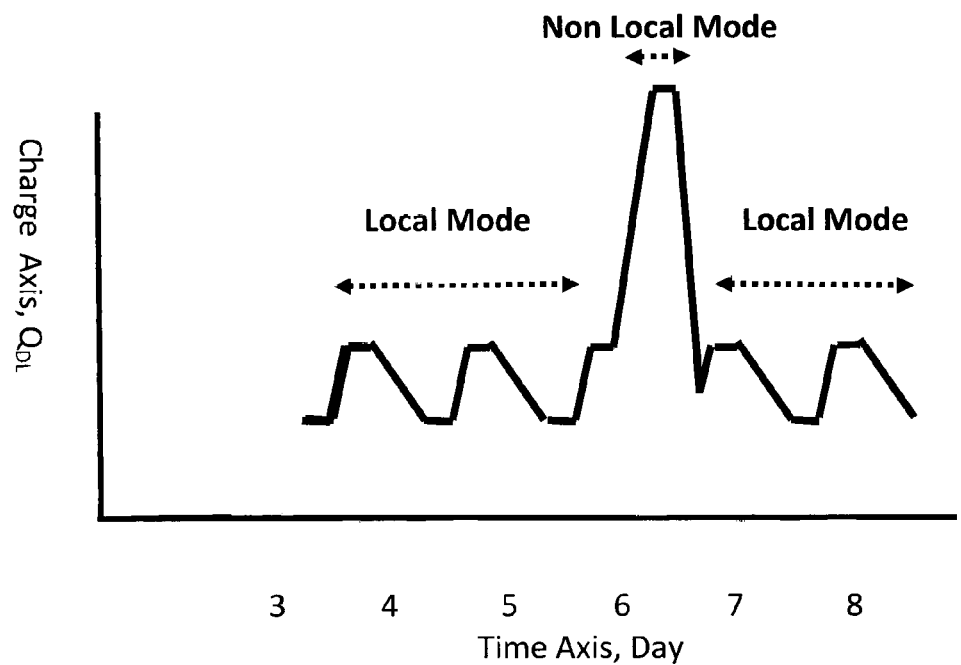
FIG. 3c Schematic diagram of the total adsorbed ion population in a local and non local mode. The local mode ensues during time periods wherein the total ion population is set by ions in the vicinity of surface1. The non local mode ensues when ions move into the vicinity of surface1 from regions remote from surface1. The non local mode occurs during periods of irrigation and/or nutrient uptake.
Figure 3D:
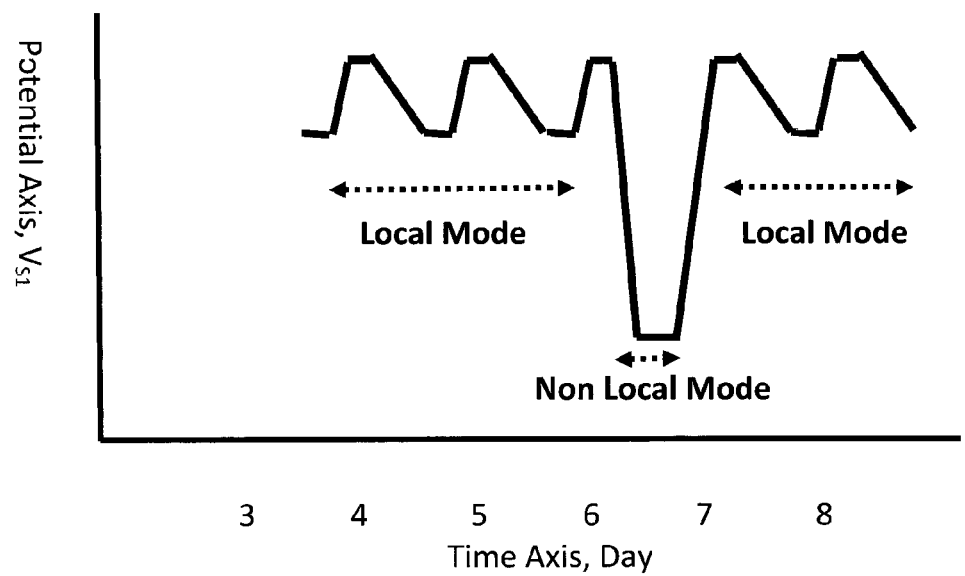
FIG. 3d Quiescent potential shift during local and non local lodes. This shift is a manifestation of the change in ion composition.
Figure 3E:
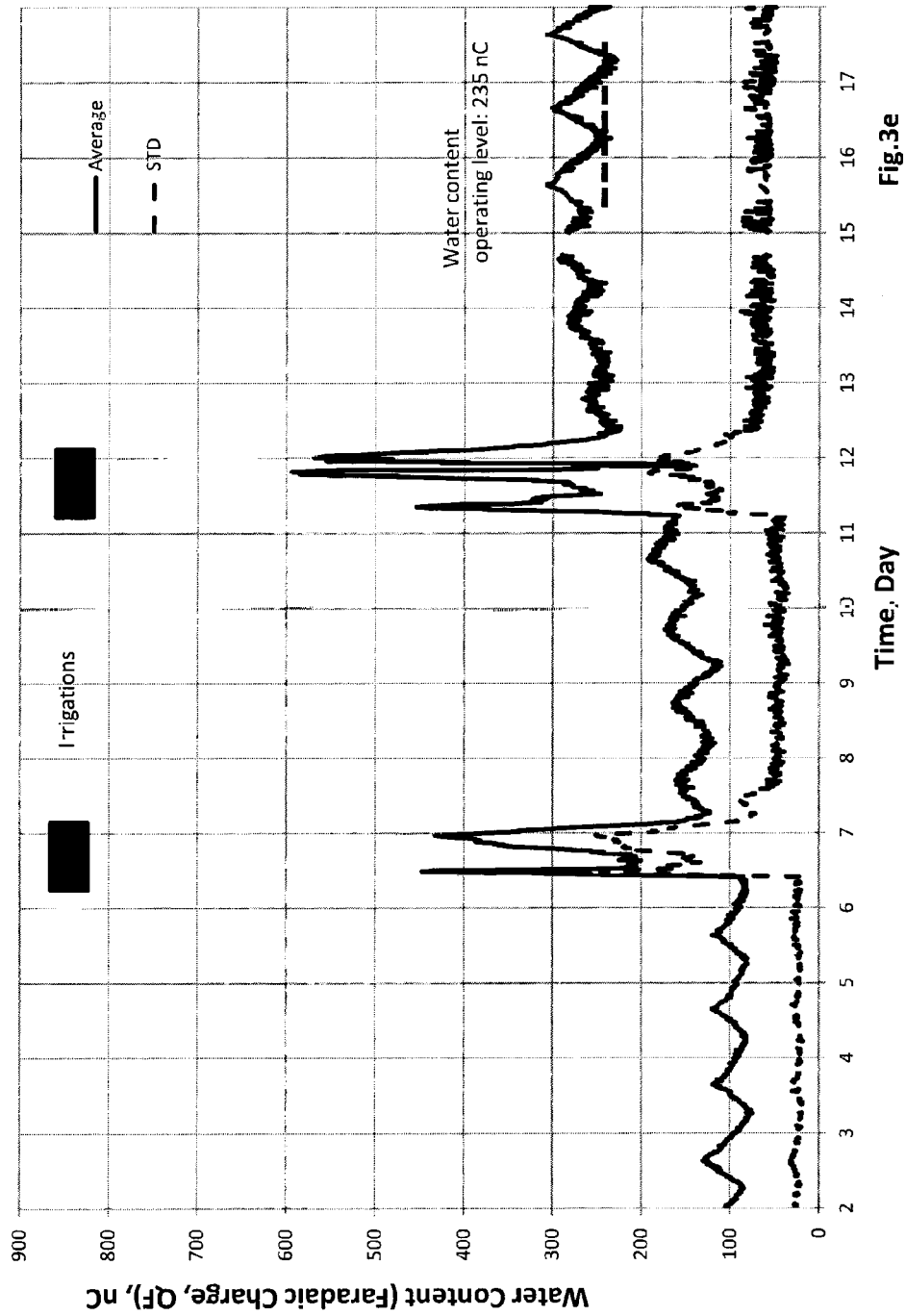
FIG. 3e Example of the sapwood water content response to irrigation in the post harvest period in almonds. Irrigation was limited in the harvest period to harden the ground prior to harvest machinery operations. Post harvest the trees responded to water application as seen in increases in the water content level, $Q_F$.
Figure 3F:
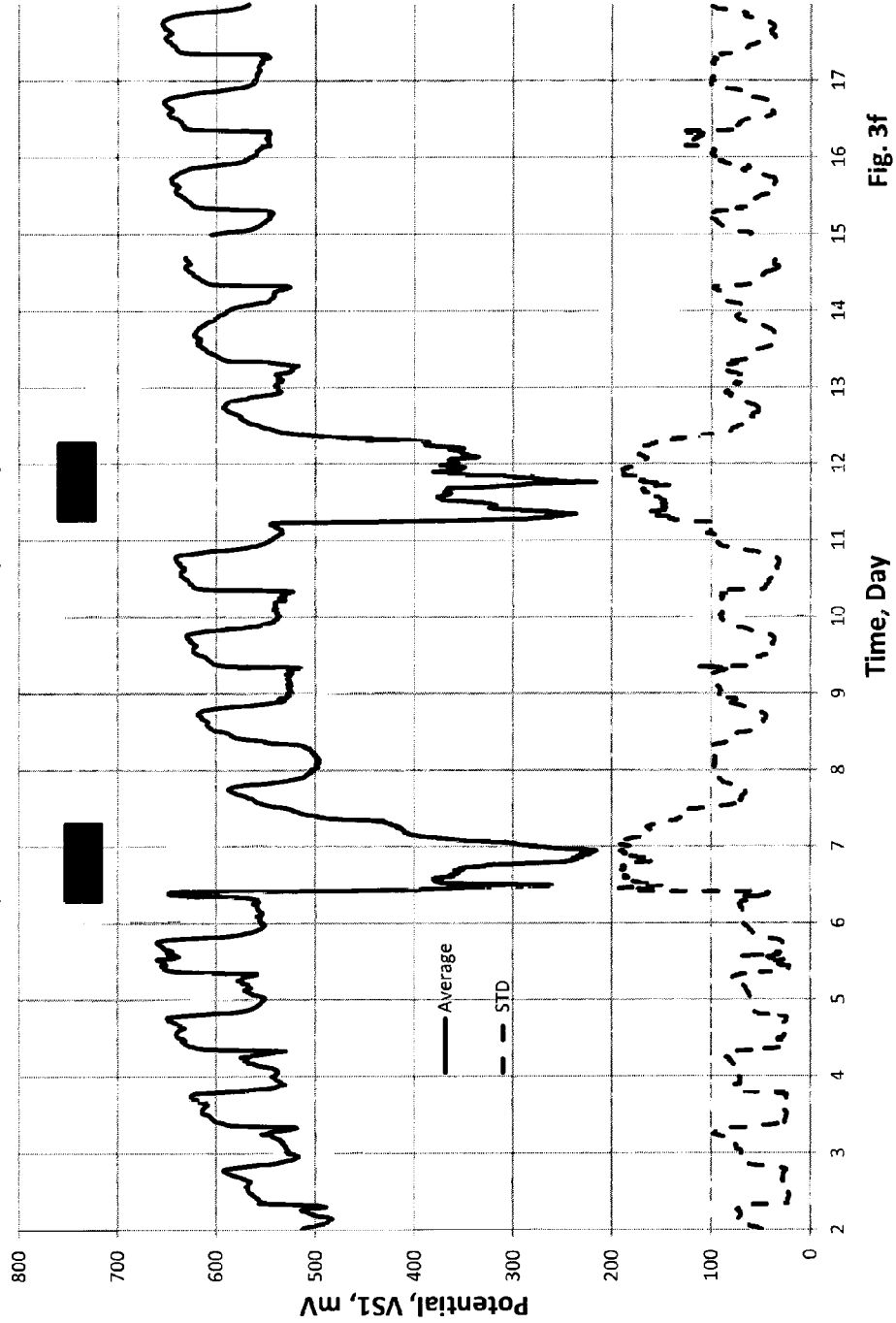
FIG. 3f Example of sapwood quiescent potential in the post harvest period in almonds. Quiescent potential response was muted and limited to the period of water application.

FIG. 3h Example of the quiescent potential during irrigation cycles in avocados. The diurnal cycles followed putative nitrate response wherein the potential would decrease at night concomitant with an uptake of an increase in the presence of anions.

Figure 4A:
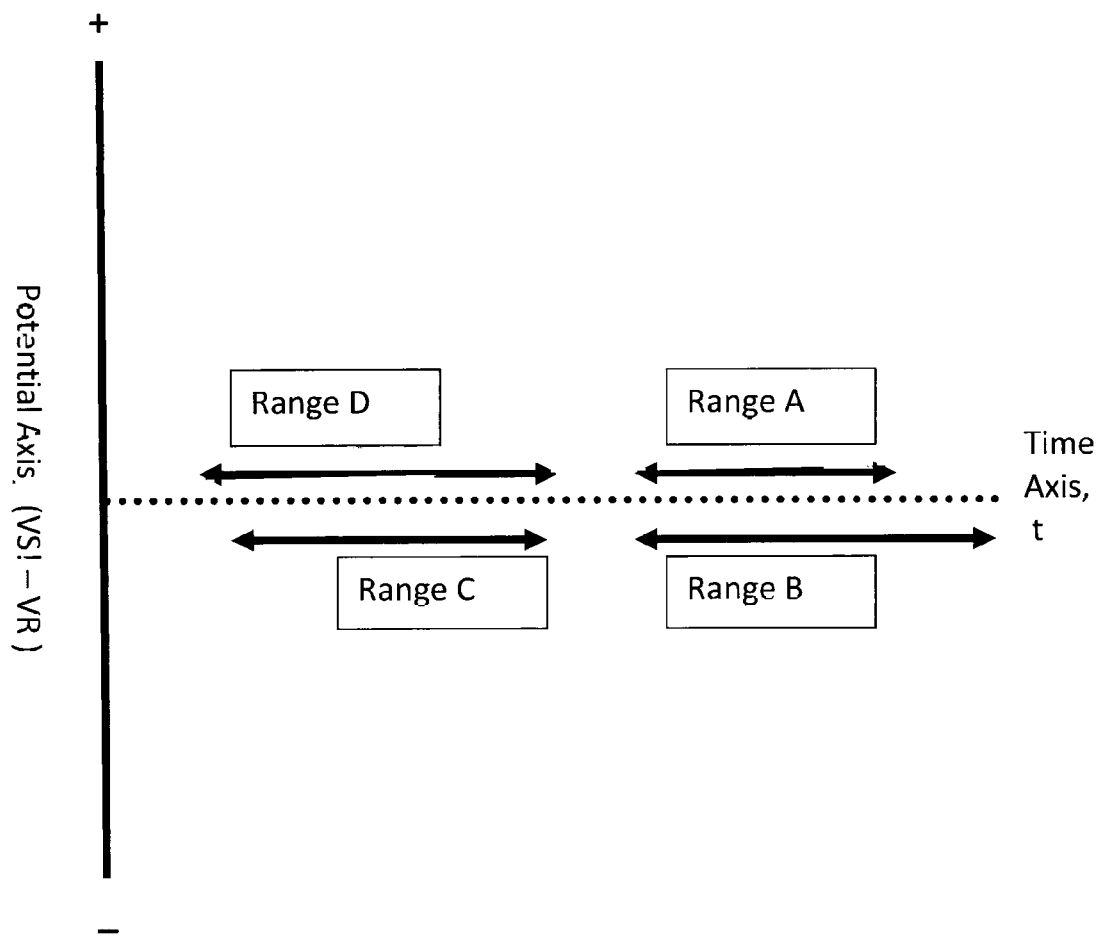

FIG. 4a Schematic diagram of the division of the potential/time plot into four time ranges. Presence of the time/potential measurement pairs in a range indicates the presence of the ion type characteristic of that range.

FIG. 4b Example of the potential/time response due to application of guano fertilizer in citrus. Uptake was distinctly channeled into particular time periods.

FIG. 4c Example of the potential/time response due to application of phosphoric acid in pecans. Uptake was distinctly channeled into particular time periods. In addition, there was residual uptake of nitrate during post application days.

OPERATIONAL ASPECTS

Figure 1A:
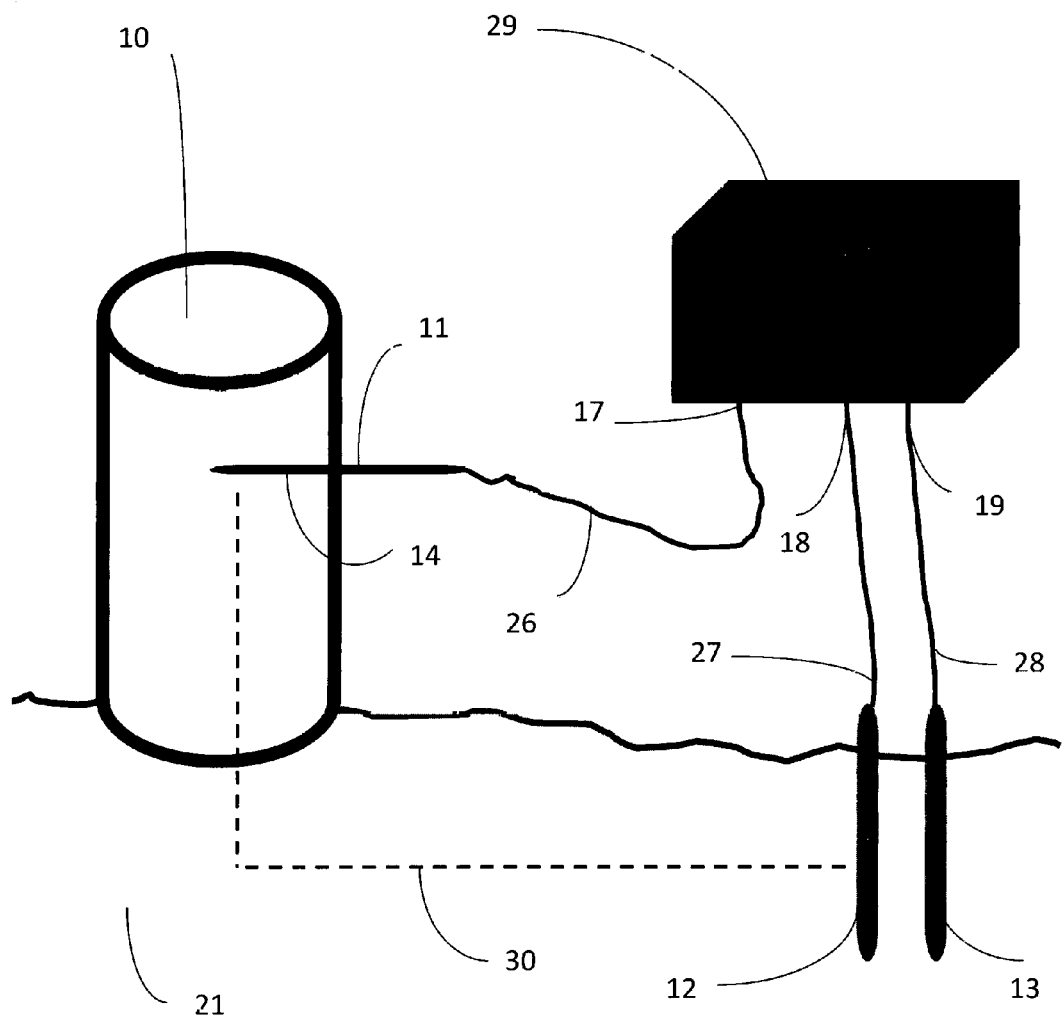
FIG. 1a Components of the Electrochemical Circuit Provided for in the Method. The quintessential component is interface1 (14). Surface3 13 is employed to reference surface1 to the standard hydrogen electrode.

FIG. 1a shows the basic components of the method. Surface1 11 is located inside plant 10. First wire 26 connects electronics 29 to surface1 11. Second wire 27 connects electronics 29 to the surface2 12 located in root zone 21. The electrochemical circuit path is from terminal 17 of electronics 29 connected to first wire 26, to surface1 11, across interface1 14 through plant 10, through root zone 21, across interface2, through second wire 27 connected to terminal2 18 of electronics 29.

Electrochemical Procedures
Measurement of the Quiescent Potential

The method provides for the apparatus shown in FIG. 1a. The first electrochemical procedure begins with the electronics 29 functioning as a voltmeter. Electronics 29 measures the potential between terminal1 17 with respect to terminal2 18. The result is a value of M1 given in Eqn. 1. The potential of terminal3 19 with respect to terminal 18 is measured. The result is a value of M2 given in Eqn. 2 These potential values are entered into Eqn. 6 to produce the adjusted value of $V_{S1}$. The value of M3 is set by the manufacturer of the surface M3.

An adjusted or unadjusted value of $V_{S1}$ can be used in Electrochemical Procedure #2.

Figure 2A:
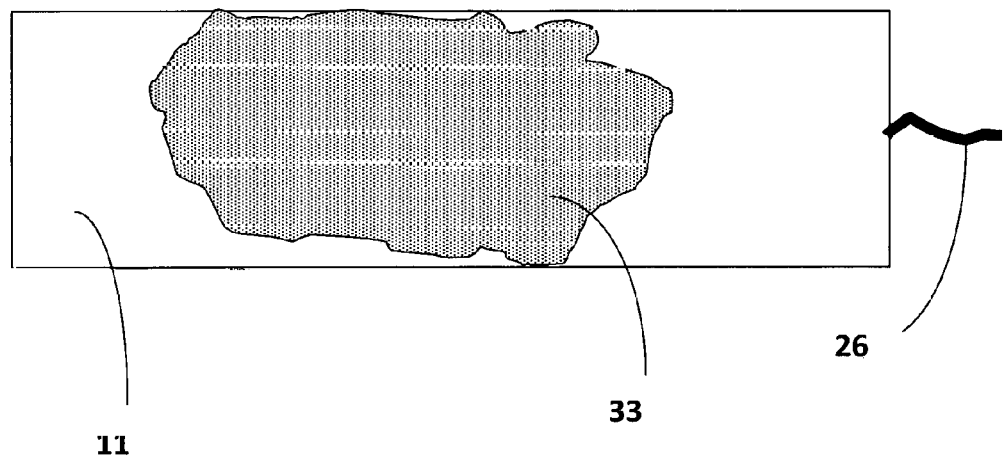
FIG. 2a Schematic diagram of a part of surface1 11 wetted by the extracellular fluid FIG. 2b Schematic diagram of interface1 (14). A layer of electrons 35 is present just inside the surface of the metal. On top of this layer is an adjacent layer of adsorbed ions 34. These two layers form the "double layer." Above the layer of adsorbed ions is the bulk (homogeneous) extracellular fluid 36. When a perturbation potential is applied to this interface, adsorbed ions 34 desorb to the bulk fluid 36 and ions in the bulk fluid 36 adsorb on the metal surface. Electrons also pass to and from the metal surface to the bulk fluid when the perturbation potential is applied.
Figure 2B:
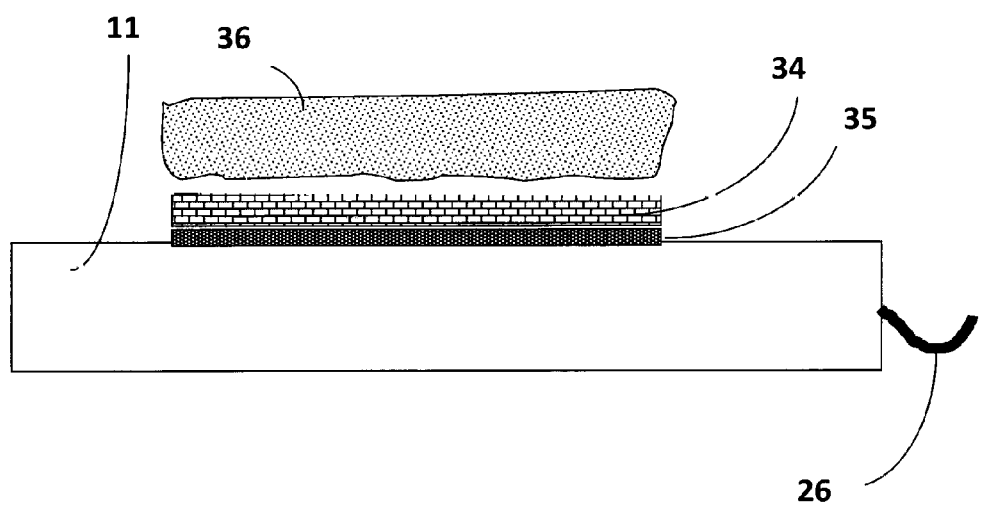
FIG. 2c Top view of the metal surface showing three examples of ion populations located in a unit area of wetted surface. The bottom unit area is dominated by anions. The top unit area is dominated by cations. The middle unit area is charge neutral. The potential axis shown on the left indicates the relative energy level of the ion populations in the three unit areas.
FIG. 2d Illustration of the reconfiguration in the adsorbed ion population within a unit area of wetted surface due to a positive perturbation potential. The lower square shows the population at quiescent potential. The top square shows the population after the perturbation potential is applied.
FIG. 2e Example of the sequence of measured charge transfer values following application of a perturbation potential. The measured charge transfer $Q_M$ (diamond symbol) rises and gradually takes on a constant slope. The measured charge transfer comes from two sources: double layer charge $Q_{DL}$ reconfiguration (square symbol) and electrons $Q_F$ crossing the interface (triangle symbol). The double layer charge transfer rises exponentially; the electron charge transfer rises in a linear manner.
Figure 2C:
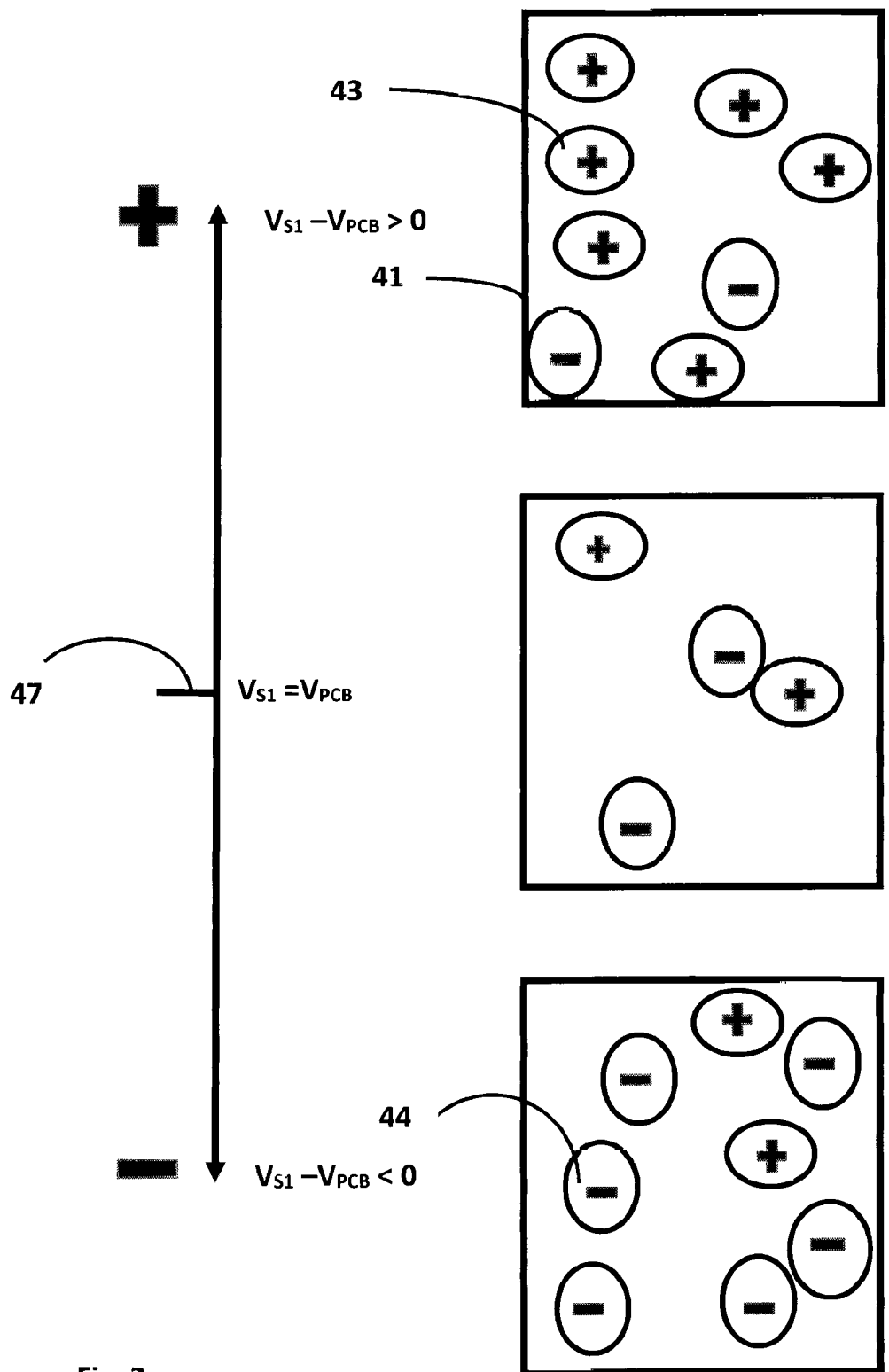
Figure 2D:
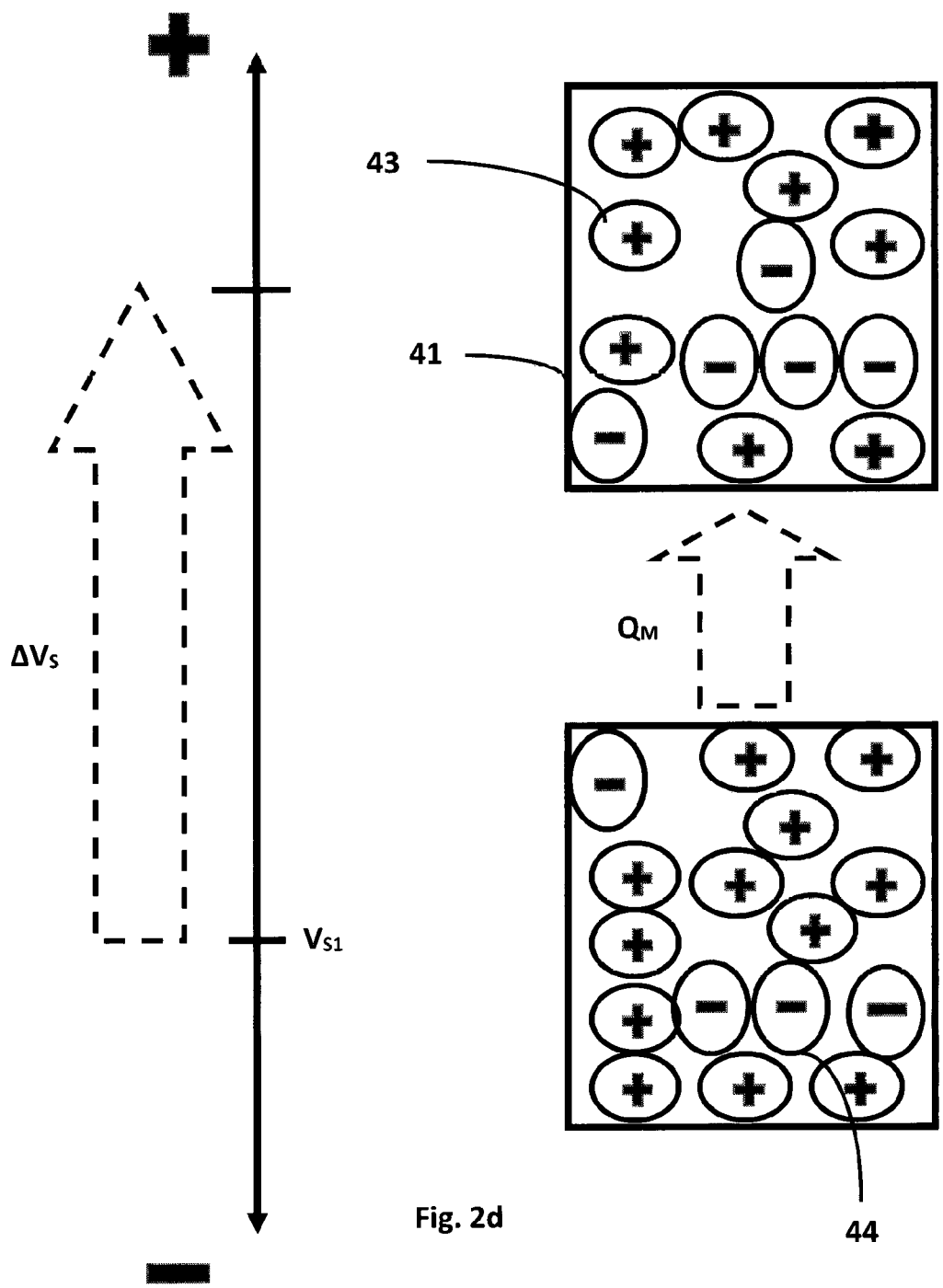
Figure 2E:
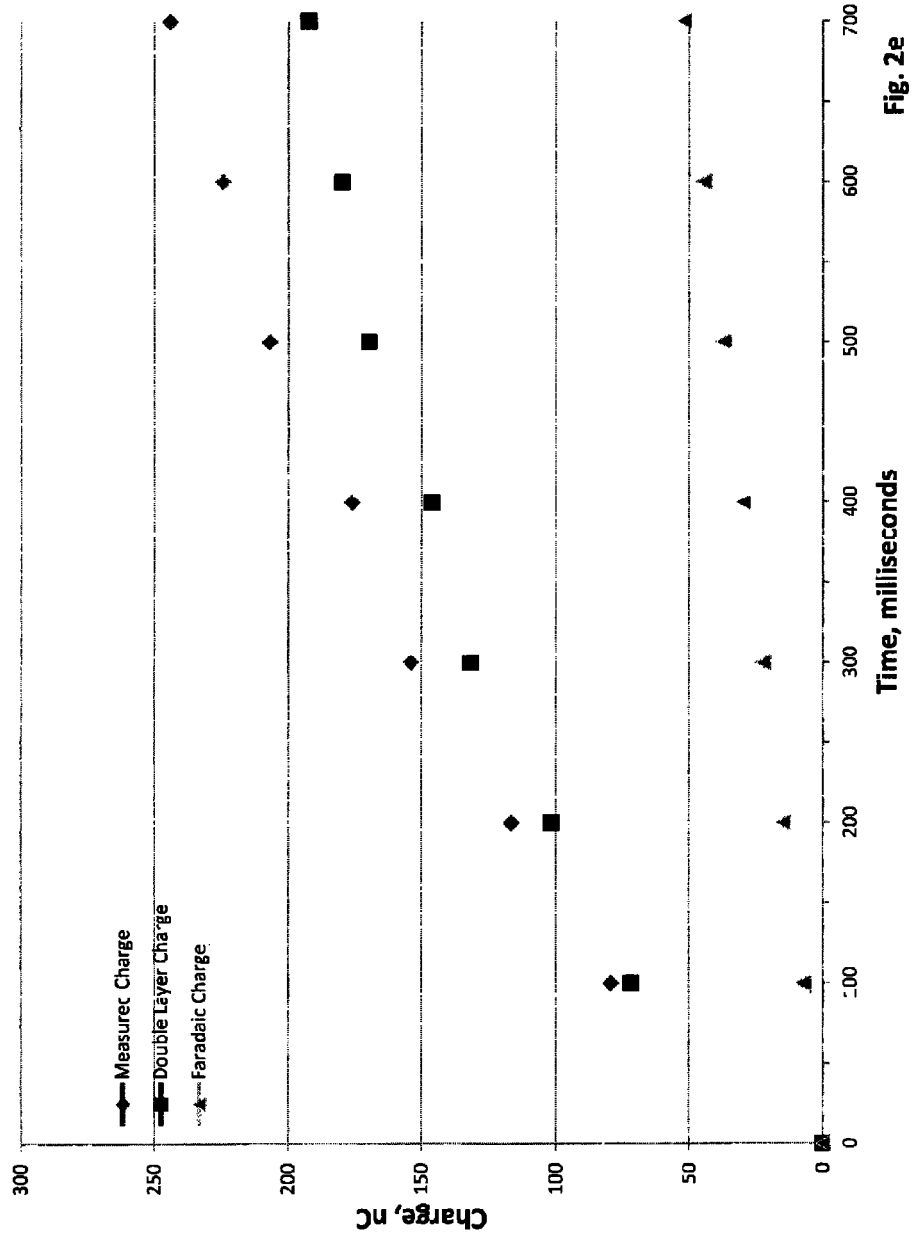

Electrochemical Procedure #2: Measurement of Charge Values Electronics 29 computes a potential Vs1+ΔVs1. The perturbation potential is ΔVs1. It is defined in Eqn. 1 or Eqn. 6. Electronics 29 now functions as a potential source. A potential is applied between terminal1 17 and terminal2 18 for time interval1. Charge transfer occurs through first wire 26 and second wire 27 during time interval1. The cumulative charge transfer is measured periodically. An example of these periodic measurements is given in FIG. 2e. Values of cumulative charge transfer are $Q_{M1}$, $Q_{M2}$ . . . . These values form the sequence of charge transfer valuesM. The value $Q_{MT1}$ is the cumulative charge transfer at the end of the time interval1. Electronics 29 functions as a charge measuring device.

Relation of the Four Parts of the Method as Described in the Specification to the Steps in the Claims Table 1 gives a correlation of the Four Parts of the Method to the steps in the Claims.

CONCLUSIONS AND RAMIFICATIONS

Uses of the Invention

The method has been shown to be capable of: 1) determination of the amount of extracellular fluid in the tissue surrounding the surface within the plant, 2) identification of the ion types in the fluid adsorbed on the surface and 3) determination of the population of ions within this fluid.

The use of this information has direct application in irrigation and fertilizer management. The central management principle is based on plant demand. Water and fertilizer is applied when the plant wants water and/or fertilizer. It is not applied when the plant does not want water and/or fertilizer. This method is used to assess plant demand. In irrigation management the method is to set a target value of water content, $Q_F$. The value will rise and fall in a sawtooth time pattern. When the water content value declines to the target value, water is applied. The value will jump and then gradually decrease. When the value again reaches the target value, water is again applied. The result is a sawtooth pattern in time of the value of $Q_F$. In fertilizer management, a single nutrient such as nitrate is applied in a small quantity (spoon-feeding). If the plant wants the nitrate, the fluid will shift from the local mode to the non local mode. The quiescent potential will decline and the charge transfer will increase in magnitude. Nitrate is applied again until the plant does not want any more nitrate.

A Tool for Phyto-Centric Methods

The methodology of water and fertilizer application at the present time is based on supply. It is an anthropo-centric method based on the Grower's viewpoint of what the plant needs. This is a supply based method. By contrast, this method is a tool to implement a phyto-centric method. The plant tells the Grower when and how much water and fertilizer it wants. The demand on the part of the plant is assessed using the principle of immediate demand. The Grower applies only a small amount of water and/fertilizer. If the plant takes it up, the Grower supplies more. If the plant does not take it up. The Grower stops application. This method can be applied in supply based cultural practice to determine water and nutrient status. But it naturally fits with demand based cultural practice.

Minimally Disruptive Methods

This invention employs electrochemical procedures that are gentle. The procedures are limited to measurement of the quiescent potential and a sequence of charge values. When an active electrochemical procedure is employed it is only a perturbation of the quiescent condition. The influence of this perturbation is minimal if a follow on procedure restores the electrochemical status of the fluid to the conditions before execution. The specialized facets of the procedure are necessary because the implanted surface is in the same tissue for extended periods of time. There are thousands of executions per year. These procedures disrupt the metabolic activity of the tissue surrounding the surface at a near zero level.

Unifying Concept Concerning this Method: A "Blood" Test in Plants

A unifying concept concerning this method can be gained from an analogy with medicine. Hematology in medicine is the study of blood in humans. Phyto-hematology in the plant sciences is the study of the extracellular fluid of plants. The blood test in human hematology is a procedure to determine constituents of the blood. The extracellular fluid test in phyto-hematology is a procedure to determine the amount of fluid present and the identity and population of the ions in that fluid. The patient in human hematology is analogous to the plant in phyto-hematology. In human hematology the blood is an assay outside the body. In phyto-hematology the extracellular fluid is assayed (this method) while the fluid is still within the plant. An aspect of phyto-hematology (and this method) which has no direct counterpart in human hematology is the determination of the amount of extracellular fluid. Dehydration and rehydration of the extracellular fluid volume is a very common occurrence in phyto-hematology. The amount of extracellular fluid is changing constantly. Changes in the amount of blood in the human body are not a normal occurrence. The procedures in this method can be viewed as analogous to procedures and results in human hematology. This comparison will enhance understanding of the methods and utility of these procedures.

Time Scales of this Method

This method operates at two widely different time scales: a short time scale in the order of hundreds of milliseconds, during which two electrochemical procedures are executed and a long time scale, in the order of hours, days and weeks, during which these procedures are executed multiple times.

Space Scales of this Method

This method operates over two widely different space scales: a very small scale in the order of nanometers at interface1 and very large scale in the order tens of meters between the electronics and the surface in the plant. The wire from the electrochemical circuit may be many meters in length, but the salient electron and ion transfers occur over a distance of nanometers at the end of the wire at the surface inside the plant.

Scope of Method

Although the description above contains many specificities, these should not be construed as limiting the scope of the method, but as merely providing illustrations of some of the presently preferred embodiments of this method. For example, the measurements are potential measurements and changes in adsorbed charge and electrons crossing interface1. An alternate embodiment could be measurements of potential and charge That crosses the interface due to a step function or ramp function of current. Thus the scope of the method should be determined by the appended claims and their legal equivalents, rather than the examples given.

AN ALTERNATE EMBODIMENT

Surface2 12 is located in the root zone in FIG. 1b. It is possible to dispose surface2 such that both surface1 and surface2 are inside the plant. Two wires would extend out of the plant from these surfaces. The method described herein would be the same.

I claim:

1. A method for measuring within a plant the amount of extracellular fluid surrounding surface1 disposed within said plant, the ion population of said extracellular fluid and the identity of the dominant ion in said ion population comprised of,
   (a) disposing surface1 within said plant whereby interface1 is formed between said surface1 and said extracellular fluid,
   (b) disposing surface2 within the root zone of said plant whereby interface2 is formed between said surface2 and said root zone,
   (c) providing for electronics containing terminal1 and terminal2 such that said electronics is able to measure potential across said terminal1 and said terminal2, provide a potential between said terminal1 and said terminal2 and measure charge transfer across said terminal2,
   (d) providing for a wire1 connecting said surface1 and said terminal1 of said electronics,
   (e) providing for a wire2 connecting said surface2 and said terminal2 of said electronics,
   (f) measuring a potential1 of said terminal1 with respect to said terminal2 of said electronics wherein there is no charge transfer through said terminal 2,
   (g) providing for a potentialP between said terminal1 and said terminal2 for time interval1 wherein the value of said potentialP is equal to the value of said potential1 plus incremental value1 whereby charge transferM occurs across said terminal1,
   (h) measuring said charge transferM at fixed time intervals during said time interval1 whereby sequence of charge transfer valuesM is generated,
   (i) forming a sequence of charge transfer valuesF such that the values of said sequence of charge transfer valuesF increases during said time interval1 in a linear manner wherein the rate of increase of said sequence of charge transfer valuesF is equal to rate of increase of said sequence of charge transfer valuesM at the end of said time interval1 whereby the value of said sequence of charge transfer valuesF at time T3 is proportional to said amount of extracellular fluid,
   (j) forming sequence of charge transfer valuesDL such that the value of said sequence of charge transfer valuesDL is equal respectively to the value of said sequence of charge transfer valuesM minus said value of said sequence of charge transfer valuesF at said fixed time intervals whereby the value of said sequence of charge transfer valuesDL at the end of said time interval1 is proportional to said ion population of said extracellular fluid,
   (k) forming sequence of charge transfer valuesE wherein said sequence of charge transfer valuesE is an exponential function with adjustable final valueE and time constantE,
   (l) setting said final valueE to value of said sequence of charge valuesDL at the end of said time interval1,
   (m) adjusting said time constantE to match the respective values of said sequence of charge valuesE with said sequence of charge transfer valuesDL whereby the value of said time constantE identifies said dominant ion in said extracellular fluid surrounding said surface1.

2. A method for determining the presence of specific ion types in the extracellular fluid surrounding surface1 disposed within a plant comprised of
   (a) disposing said surface1 in said plant whereby interface1 is formed between said surface1 and said extracellular fluid,
   (b) disposing surface2 within the root zone of said plant whereby interface2 is formed between said surface2 and said root zone,
   (c) providing for electronics containing terminal 1 and terminal2 such that said electronics is able to measure potential1 of said terminal1 with respect to said terminal2,
   (d) providing for wire1 connecting said surface1 and said terminal1 of said electronics,
   (e) providing for wire2 connecting said surface2 and said terminal2 of said electronics, (f) predetermining a reference potential value, an onset time and a termination time wherein said reference potential value will be constant in the time interval between said onset time and said termination time,
(g) measuring at fixed time intervals within said onset time and said termination time a potential of said terminal1 with respect to said terminal2 of said electronics wherein there is no charge transfer through said terminal2 wherein a set of time potential pairs consisting of time valueX and potential valueX are generated,
(h) predetermining groupA, groupB, groupC and groupD,
(i) dividing said time interval between said onset time and said termination time into time rangeA, time rangeB, time rangeC and time rangeD wherein said time rangeB and said time rangeC are mutually exclusive in said time interval between said onset time and said termination time and said time rangeA and said time rangeD are mutually exclusive in said time interval between said onset time and said termination time,
(j) placing each member of said set of time potential pairs into groupA if said time valueX is within said time rangeA and said potential valueX is greater than said reference potential,
(k) placing each member of said set of time potential pairs into groupB if said time valueX is within said time rangeB and said potential valueX is less than than said reference potential,
(l) placing each member of said set of time potential pairs into groupC if said time valueX is within said time rangeC and said potential valueX is less than said reference potential,
(m) placing each member of said set of time potential pairs into groupD if said time valueX is within said time rangeD and said potential valueX is greater than said reference potential,
(n) in step (j), replacing said potential valueX in each said time potential pair in said groupA with sumAX value wherein said sumAX value is the total of said potential valueX minus said reference potential,
(o) in step (n), adding together said sumAX values in said groupA wherein total sumA is generated whereby said total sumA indicates the presence of ion type A,
(p) in step (k), replacing said potential valueX in each said time potential pair in said groupB with sumBX value wherein said sumBX value is the total of said potential valueX minus said reference potential,
(q) in step (p), adding together said sumBX values in said groupB wherein total sumB is generated whereby said total sumB indicates the presence of ion type B,
(r) in step (l), replacing said potential valueX in each said time potential pair in said groupC with sumCX value wherein said sumCX value is the total of said potential valueX minus said reference potential,
(s) in step (r), adding together said sumCX values in said groupC wherein total sumC is generated whereby said total sumC indicates the presence of ion type C,
(t) in step (m), replacing said potential valueX in each said time potential pair in said groupD with sumDX value wherein said sumDX value is the total of said potential valueX minus said reference potential,
(u) in slop (t), adding together said sumDX values in said groupD wherein total sumD is generated whereby said total sumD indicates the presence of ion type D.

\* \* \* \* \*